(12) United States Patent
Nishiguchi

(10) Patent No.: US 8,940,658 B2
(45) Date of Patent: Jan. 27, 2015

(54) CATALYST FOR PRODUCING UNSATURATED CARBOXYLIC ACID AND A PROCESS FOR PRODUCING UNSATURATED CARBOXYLIC ACID USING THE CATALYST

(75) Inventor: Toshiya Nishiguchi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 119 days.

(21) Appl. No.: 13/990,513

(22) PCT Filed: Sep. 26, 2011

(86) PCT No.: PCT/JP2011/071804
§ 371 (c)(1),
(2), (4) Date: May 30, 2013

(87) PCT Pub. No.: WO2012/073584
PCT Pub. Date: Jun. 7, 2012

(65) Prior Publication Data
US 2013/0253223 A1 Sep. 26, 2013

(30) Foreign Application Priority Data

Dec. 3, 2010 (JP) ................................. 2010-270069

(51) Int. Cl.
| | | |
|---|---|---|
| *B01J 27/228* | (2006.01) | |
| *B01J 35/06* | (2006.01) | |
| *B01J 23/00* | (2006.01) | |
| *B01J 23/28* | (2006.01) | |
| *B01J 23/887* | (2006.01) | |
| *B01J 23/888* | (2006.01) | |
| *B01J 35/02* | (2006.01) | |
| *B01J 37/02* | (2006.01) | |
| *C07C 51/235* | (2006.01) | |
| *C07C 51/25* | (2006.01) | |

(52) U.S. Cl.
CPC .............. *B01J 27/228* (2013.01); *B01J 23/002* (2013.01); *B01J 23/28* (2013.01); *B01J 23/8877* (2013.01); *B01J 23/8885* (2013.01); *B01J 35/023* (2013.01); *B01J 35/06* (2013.01); *B01J 37/0221* (2013.01); *C07C 51/235* (2013.01); *C07C 51/252* (2013.01); *B01J 2523/00* (2013.01)

USPC ........................................................ 502/312

(58) Field of Classification Search
None
See application file for complete search history.

(56) References Cited

U.S. PATENT DOCUMENTS

| | | |
|---|---|---|
| 2004/0030185 A1 | 2/2004 | Hirao et al. |
| 2005/0008842 A1 | 1/2005 | Peduto et al. |
| 2006/0063951 A1 | 3/2006 | Yunoki et al. |
| 2009/0043128 A1 | 2/2009 | Yunoki et al. |

FOREIGN PATENT DOCUMENTS

| | | |
|---|---|---|
| EP | 1 852 406 | 11/2007 |
| EP | 1 982 762 | 10/2008 |
| JP | 60-150834 | 8/1985 |
| JP | 7-251075 | 10/1995 |
| JP | 9-52053 | 2/1997 |
| JP | 2004-243213 | 9/2004 |
| JP | 2004-351297 | 12/2004 |
| JP | 2010-201401 | 9/2010 |
| WO | 2009/052274 | 4/2009 |

OTHER PUBLICATIONS

Extended European Search Report issued Jul. 11, 2014 in corresponding European Application No. 11844503.0.
International Search Report issued Dec. 6, 2011 in corresponding International (PCT) Application No. PCT/JP2011/071804.
English abstract of JP 6-150834.
English abstract of JP 7-251075.
International Preliminary Report on Patentability issued Jun. 4, 2013 and English translation of Written Opinion of the International Searching Authority issued Dec. 6, 2011 in International Application No. PCT/JP2011/071804.

*Primary Examiner* — Yevegeny Valenrod
(74) *Attorney, Agent, or Firm* — Wenderoth, Lind & Ponack, L.L.P.

(57) ABSTRACT

Provided is a catalyst for producing unsaturated carboxylic acid, which excels in mechanical strength and attrition loss and is capable of producing the object product at a high yield. This catalyst is formed of a catalytically active component comprising molybdenum and vanadium as the essential ingredients and inorganic fibers, which are supported on an inert carrier, said catalyst being characterized in that said inorganic fibers comprise at least an inorganic fiber having an average diameter less than 1.0 μm and another inorganic fiber having an average diameter ranging from 1.5 to 7 μm.

8 Claims, No Drawings

CATALYST FOR PRODUCING UNSATURATED CARBOXYLIC ACID AND A PROCESS FOR PRODUCING UNSATURATED CARBOXYLIC ACID USING THE CATALYST

TECHNICAL FIELD

This invention relates to a catalyst for producing unsaturated carboxylic acid, more specifically, to a catalyst suitable for producing unsaturated carboxylic acid by catalytic vapor-phase oxidation of unsaturated aldehyde or saturated hydrocarbon in the presence of molecular oxygen. The invention also relates to a process for producing unsaturated carboxylic acid using the catalyst.

BACKGROUND ART

Unsaturated carboxylic acids such as acrylic acid, methacrylic acid and the like are industrially important, as starting materials for various synthetic resins, coatings, plasticizing agents and the like. In particular, the importance of acrylic acid as a starting material for water-absorbent resin has been increasing in late year. As production processes for unsaturated carboxylic acids such as acrylic acid and methacrylic acid, referring to acrylic acid for example, the most commonly practiced is the two-stage oxidation method comprising producing acrolein first by catalytic vapor-phase oxidation of propylene, and then producing acrylic acid by catalytic vapor-phase oxidation of the acrolein. Whereas, development of single-stage oxidation of propane to produce acrylic acid is also advanced in recent years, because propane is cheaper than propylene, and various proposals were made concerning the technology. Also about industrial manufacture of methacrylic acid, known is a two-stage oxidation method comprising first producing methacrolein through catalytic vapor-phase oxidation of at least one starting material selected from isobutylene, t-butanol and methyl-t-butyl ether and then producing methacrylic acid through further catalytic vapor-phase oxidation of the resulting methacrolein.

As the catalysts useful in such catalytic vapor-phase oxidation of unsaturated aldehydes such as acrolein or methacrolein, or saturated hydrocarbons such as propane in the presence of molecular oxygen to make corresponding unsaturated carboxylic acids such as acrylic acid and methacrylic acid, those containing molybdenum and vanadium are widely known. Improvements in not only the yield of the object product but in mechanical strength of the catalysts which is required in the occasions of their industrial use are challenged in the concerned art, and many proposals have been made for the purpose of improving the mechanical strength without impairing yields of the object products.

Such past proposals include, for example, a catalyst obtained by molding and calcining a dry material obtained of a liquid mixture of starting materials, in which the ignition loss ratio of the dry material ranges 5-40 mass % (cf. JP 2004-243213A); an extrusion-molded catalyst containing 0.5-5 wt % of graphite (cf. JP 60 (1985)-150834A); a catalyst containing 0.05-10 wt % of a carbon fiber having an average diameter of 1-20 μm, average length of 10-3,000 μm and a carbon content of at least 93% (cf. JP 7 (1995)-251075A); or a catalyst produced by mixing a precursor of an oxide and the oxide, and calcining the same (JP 2004-351297A).

SUMMARY OF THE INVENTION

The Problems to be Solved by the Invention

Catalysts for use in production of unsaturated carboxylic acid by catalytic vapor-phase oxidation of unsaturated aldehyde or saturated hydrocarbon are generally in the forms of molded catalyst provided by molding the catalytically active component only, into a fixed shape, or supported catalyst provided by having an inert carrier support the catalytically active component. From the viewpoint of reducing thickness of the catalyst layer whereby suppressing side reactions induced by successive oxidation of the object product, supported catalyst is preferred.

On the other hand, a supported catalyst has a defect due to its structure that the catalytically active component is supported on an inert carrier. For example, the catalytically active component is apt to flaked off of the inert carrier under an impact exerted in the occasion of packing the catalyst in a reaction tube by dropping. That is, a supported catalyst has low mechanical strength. A catalyst of low mechanical strength gives rise to such problems as increase in pressure loss or plugging of reaction tubes, caused by the catalytically active component flaked off in the occasion of packing the reaction tube. Therefore, further improvement in mechanical strength is desired for supported catalysts.

Separately from the above mechanical strength, it is also desirable to suppress whittling and attrition of catalyst surfaces by their mutual contact or by friction between the catalyst and wall surfaces, which take place in the operations for the catalyst preparation such as canning, transportation and packing (this phenomenon is hereafter referred to as "attrition loss"). Control of the attrition loss is very important, in consideration of the economical problem that the resulting catalyst powder brings about an increase in pressure loss and loss of catalytically active component, health problem that the workers are exposed to the catalyst powder which flies about during the catalyst packing operation, and the environmental problem that such catalyst powder is scattered into the air.

While all of the catalysts proposed in the past as referred to in the above show mechanical strength and attrition loss improved to a certain extent, their effects are not yet fully satisfactory, and a catalyst which enables high yield production of the object product and, at the same time, still more favorable mechanical strength and attrition loss, is in demand.

The object of the present invention is to solve the above problem in the conventional technology, and to provide a supported catalyst suitable for production of unsaturated carboxylic acid by catalytic vapor-phase oxidation of unsaturated aldehyde or saturated hydrocarbon in the presence of molecular oxygen, more specifically, a supported catalyst which excels in mechanical strength and attrition loss, and is capable of producing the object product at a high yield.

Means to Solve the Problem

We have engaged in concentrative studies of molybdenum-vanadium-containing supported catalyst for producing unsaturated carboxylic acid by catalytic vapor-phase oxidation of unsaturated aldehyde or saturated hydrocarbon in the presence of molecular oxygen, with the view to improve its mechanical strength and to suppress the attrition loss, and have come to discover that both the mechanical strength and the attrition loss can be improved by having the catalyst contain, concurrently with the catalytically active component, at least two kinds of inorganic fibers differing in average diameter, and that the catalyst is capable of producing the object product at a high yield.

More specifically, we discovered that a catalyst in which a catalytically active component comprising molybdenum and vanadium as the essential ingredients, and the inorganic fibers are supported on an inert carrier, said inorganic fibers comprising at least an inorganic fiber having an average diameter less than 1.0 μm and another inorganic fiber having an average diameter ranging from 1.5 to 7 μm, excels in both mechanical strength and attrition loss and can produce the object product at a high yield.

We have also discovered that the detrimental effect of the inorganic fibers on the catalytic performance could be suppressed by setting the total content of the inorganic fibers to be from 0.5 to 30 mass % to the catalytically active component.

Effect of the Invention

Thus, according to the invention, provided is a supported catalyst for producing unsaturated carboxylic acid by catalytic vapor-phase oxidation of unsaturated aldehyde or saturated hydrocarbon in the presence of molecular oxygen, which excels in mechanical strength and attrition loss and is capable of producing the object product at a high yield.

Embodiments for Working the Invention

Hereinafter the catalyst for producing unsaturated carboxylic acid and the process for producing unsaturated carboxylic acid with use of said catalyst of the present invention are explained in details, it being understood that the scope of this invention is not restricted by the explanations and that any of the specific embodiments hereinafter exemplified can be suitably modified within the limit not impairing the purpose of this invention.

The catalyst for production of unsaturated carboxylic acid according to the present invention is formed of a catalytically active component comprising molybdenum and vanadium as the essential ingredients and inorganic fibers, which are supported on an inert carrier. It is important that the inorganic fibers comprise at least one inorganic fiber having an average diameter less than 1.0 μm and another inorganic fiber having an average diameter ranging from 1.5 to 7 μm. As the catalytically active component, a catalytically active component represented by the following general formula (1) is suitable:

(1)

(wherein Mo is molybdenum; V is vanadium, A is at least an element selected from tungsten and niobium; B is at least an element selected from chromium, manganese, iron, cobalt, nickel, copper, zinc and bismuth; C is at least an element selected from antimony, tin, tellurium and phosphorus; D is at least an element selected from silicon, aluminum, titanium, cerium and zirconium; and O is oxygen; a, b, c, d, e and x stand for the respective atomic ratios of V, A, B, C, D and O, where $0<a\leq14$, $0\leq b\leq12$, $0\leq c\leq6$, $0\leq d\leq6$, and $0\leq e\leq50$ and x is a numerical value determined by the oxidized state of each of the elements).

According to the invention, as the inorganic fiber having an average diameter less than 1.0 μm, the one having an average diameter less than 0.7 μm is particularly preferred, and as the inorganic fiber having an average diameter ranging from 1.5 to 7 μm, the one having an average diameter ranging from 2 to 5 μm is particularly preferred.

Such an inorganic fiber having an average diameter less than 1.0 μm, preferably less than 0.7 μm, is assumed to work effectively for reducing the attrition loss in main, as it keeps back the powder on the catalyst surfaces because of its fine size. Whereas, the relatively thick inorganic fiber having an average diameter between 1.5 and 7 μm, preferably between 2 and 5 μm, is assumed to effectively work for improving mechanical strength in main, by binding the carrier surface and the catalytically active component. In the present invention, it is important that the catalyst contains at least two kinds of inorganic fibers differing in average diameter. With either of one kind of the fibers alone, it is difficult to simultaneously improve both the mechanical strength and attrition loss, and in consequence the mechanical strength or attrition loss left out unimproved comes to adversely affect the catalyst's performance.

As above, the concurrent presence of at least two kinds of inorganic fibers differing in average diameter is important for simultaneous improvements in the two features of mechanical strength and attrition loss. Furthermore, for the full exhibition of their effects, preferably the difference in average diameters of the two kinds of inorganic fibers lies within a certain range, for example, from 0.5 to 6.5 μm, in particular, from 1.0 to 4.5 μm. Materials of the inorganic fibers are not particularly limited and, for example, various whiskers, ceramic fibers, glass fibers, carbon fibers, mineral fibers, metal fibers and the like can be used. Their crystalline structure may be either polycrystalline, monocrystalline or amorphous. Those at least two kinds of inorganic fibers may be of a same material or of different materials, which can be suitably selected for the use as long as their average diameters meet the aforesaid respective requirements.

According to the invention, average length of the inorganic fibers is not particularly limited. Whereas, in consideration of their dispersibility in the catalyst, it is preferably within a range of from 1 to 1,000 μm, in particular, from 10 to 500 μm. Whereas, even such an inorganic fiber having an average length exceeding 1,000 μm can be conveniently used, when it is cut to have an average length falling within the prescribed range by potent agitation with a homogenizing mixer or the like.

Respective contents of those at least two kinds of inorganic fibers are suitably within a range of from 0.5 to 20 mass % each to the catalytically active component, in view of their improving effect on the mechanical strength and/or attrition loss and catalytic performance, in particular, the catalyst life. The total content of the inorganic fibers preferably lies between 0.5 and 30 mass %, to the catalytically active component. When it is less than the above-specified range, the improvement in mechanical strength and/or attrition loss is insufficient, and when it exceeds the above range, the amount of catalytically active component in the catalyst becomes relatively less, which shortens the catalyst life. Moreover, the ratio between the contents of an inorganic fiber having an average diameter less than 1.0 μm and that having an average diameter of from 1.5 to 7 μm preferably is from 1:0.2 to 1:5 on mass basis, considering that an excessive increase in either one of them results in insufficient effect of the other inorganic fiber.

The catalyst of the present invention can be prepared in accordance with any method generally used for preparation of known inert carrier-supported catalysts for unsaturated carboxylic acid production, except that the catalyst must contain at least an inorganic fiber having an average diameter less than 1.0 μm and an inorganic fiber having an average diameter between 1.5 and 7 μm, for example, by the following procedure.

First, oxide(s), hydroxide(s), ammonium salt(s), nitrate(s), carbonate(s), sulfate(s), organic acid salt(s) or the like of each of the ingredient elements, or their aqueous solutions or sols, or compound(s) containing plural elements, are made into an aqueous solution or aqueous slurry (which may hereafter be referred to as "starting material liquid mixture"), which serves as the starting material of the catalytically active component represented by the general formula (1) by, for example, mixing them with water.

The resulting starting material liquid mixture then is dried by various means such as heating or pressure reduction, where necessary, to prepare a catalyst precursor. For drying by heating, for example, such methods can be optionally used as forming a powdery dry product with a spray dryer, drum dryer or the like; making block-formed or flaky dry product using a box-type dryer or tunnel-type dryer by heating in an inert gas such as air or nitrogen, or in a gaseous current of, for example, nitrogen oxide or the like; or condensing the starting material liquid mixture once, evaporation drying the same to form solid cakes and further heat-treating the solid product as above. For the drying by pressure reduction, for example, such means as use of a vacuum dryer can be adopted, to prepare a block-formed or powdery catalyst precursor.

Thus obtained dry product is then sent to a subsequent supporting step, after optional intervening step or steps such as grinding or classification to provide a powder of adequate fineness. When occasion demands, the dry product may once be calcined and thereafter sent to the supporting step. While fineness of those powdered catalyst precursors is not particularly limited, it is preferably not more than 500 µm, in consideration of favorable supportability.

Method of adding the inorganic fibers is not particularly limited, and any can be used so long as it can uniformly disperse the inorganic fibers in the catalytically active component. For example, the fibers may be added to the starting material liquid mixture of the catalytically active component represented by the general formula (1), or to the catalyst precursor or calcinations product thereof, as obtained by drying or further calcining the starting material liquid mixture of the catalytically active component. Of those, addition and mixing of the inorganic fibers to and with the starting material liquid mixture is preferred in respect of dispersibility of the inorganic fibers. The inorganic fibers may be added in a lump or in portions, for example, in such a manner that a part thereof is added to the starting material liquid mixture, and the remainder, to the catalyst precursor which is obtained by drying or calcining the liquid mixture.

Supporting method is subject to no particular limitation and, for example, such methods as disclosed in JP 49 (1974)-11371B in which the starting material liquid mixture is deposited on an inert carrier having a fixed shape, by heating and vaporizing the liquid material under stirring, or those described in JP 64 (1989)-85139A, JP 8 (1996)-299797A or JP 2004-136267A, in which the catalyst precursor in powdered form is supported on an inert carrier, can be adopted.

Examples of the inert carrier include alumina, silica, silica-alumina, titania, magnesia, steatite, cordierite, silica-magnesia, silicon carbide, silicon nitride and zeolite. Their shape is subject to no particular limitation, any known shape such as spherical, cylindrical, ring-formed and the like being useful. Needless to say, it is unnecessary for the spherical shape to be a true sphere, but substantial sphere is satisfactory. Similarly, cylindrical or ring-formed carriers need not to have a true circular cross-section, substantially circular cross-section being satisfactory. As for those spherical, cylindrical or ring-formed carriers, their diameter D and length L can both be set between 1 and 20 mm, preferably from 2 to 14 mm, inter alia, from 2 to 9 mm, although not limited thereto. In the cylindrical or ring-formed carriers, particularly their length L preferably is from 0.5 to 2.0 times of their diameter D, more preferably from 0.7 to 1.5 times. As to the ring-formed carrier, one having a through-hole of an inner diameter ranging from 0.1 to 0.7 times of its outer diameter in the vertical direction is preferred. The ratio of the supported amount of the catalytically active component to the inert carrier is not particularly limited, while a range from 10 to 300 mass %, in particular, from 20 to 200 mass %, is preferred.

In the supporting step, a molding promoter or binder for improving supportability, a pore-forming agent for forming adequate pores in the catalyst, and the like may be used, examples of which include organic compounds such as ethylene glycol, glycerin, propionic acid, maleic acid, benzyl alcohol, propyl alcohol, butyl alcohol and phenols; and inorganic compounds such as water, nitric acid, ammonium nitrate and ammonium carbonate. They can be used either alone or in combination of two or more.

The catalyst-carrying bodies as obtained in the above supporting step are sent to the subsequent drying step and/or calcination step. In the drying step, the catalyst-carrying bodies are dried in a box-type dryer, tunnel-type dryer or the like which have been in general use, by heating in an inert gas such as air or nitrogen, or in a gaseous current of other substance such as nitrogen oxide. The drying temperature ranges from 80 to 300° C., preferably from 100 to 250° C., and the drying time preferably ranges from 1 to 20 hours.

A calcining oven to be used in the calcination step again is subject to no particular limitation, and any of generally used box-type calcination oven, tunnel-type calcination oven and the like may be used. The calcination temperature ranges from 250 to 600° C., preferably from 300 to 550° C., inter alia, from 350 to 450° C., and the calcination time preferably ranges from 1 to 20 hours. The calcination step can be suitably carried out in the air, under an air current, or in the atmosphere of an inert gas.

The calcination step is usually conducted after the drying step, while the drying step may be omitted. In case the supported catalyst is prepared using the catalyst precursor which has been calcined in advance, the calcination step is not necessarily required but aforesaid drying step alone will suffice, provided the molding promoter, binder and the like which were used in the supporting step can be eliminated thereby.

The diameter D and length L of so obtained spherical or pelletized (cylindrical or ring-formed) catalyst are not strictly limited, while they both are preferably within a range of from 3 to 15 mm each, more preferably from 3 to 10 mm. Particularly with the pelletized catalyst, its length L preferably is from 0.5 to 2.0 times of its diameter D, in particular, from 0.7 to 1.5 times. The ring-formed catalyst preferably has a through-hole having an inner diameter of from 0.1 to 0.7 times of its outer diameter in the vertical direction.

The reactor to be used in the process of this invention for producing unsaturated carboxylic acid by catalytic vapor-phase oxidation of unsaturated aldehyde or saturated hydrocarbon in the presence of molecular oxygen is subject to no particular limitation so long as it is of a fixed bed type, a fixed bed type shell-and-tube reactor being preferred. The inner diameter of the reaction tube therein is usually from 15 to 50 mm, preferably from 20 to 40 mm, inter alia, from 22 to 38 mm.

It is not necessarily required to pack each reaction tube in a shell-and-tube reactor with one, single catalyst, but each of the reaction tubes may be packed with plural kinds of catalysts. Preferred examples include a method of packing plural kinds of catalysts differing in the activity level, in such a manner that each catalyst should form a layer (hereafter referred to as "a reaction zone") (cf. JP 9(1997)-241209A and JP2003-171340A); a method in which a part of the catalyst used is diluted with an inert carrier (cf. JP 2008-528683T); or a method adopting such means in combination. In such occasions, the number of reaction zones is suitably selected according to the reaction conditions or scale of the reactor in individual case. Whereas, too many reaction zones give rise to a problem of rendering the catalyst-packing operations complex, and industrially from 2 to up to around 6 is desirable.

The reaction conditions in the invention are free from any particular restriction, and any of conditions generally used in this type of reactions may be adopted. For example, the reaction can be performed by contacting a feedstock gas which is a mixture of 1-15 vol %, preferably 4-12 vol %, of unsaturated aldehyde; 0.5-25 vol %, preferably 2-20 vol % of molecular oxygen; 0-30 vol %, preferably 0-25 vol % of steam; and balance vol % of an inert gas (e.g., nitrogen gas), with the catalyst at a temperature of 200-400° C., under a pressure of 0.1-1.0 MPa and at a space velocity of 300-5,000 hr$^{-1}$ (STP).

The grade of the feedstock gas for the reaction is free from any particular restriction. For example, acrolein-containing gas which is obtained from dehydration of glycerin or from catalytic oxidation of propane and/or propylene; and methacrolein-containing gas which is obtained from catalytic oxidation of isobutylene or tertiary butanol; and the like can be used.

EXAMPLES

Hereinafter the invention is explained more specifically, referring to working Examples, it being understood that the invention is in no way limited thereby. In the following, "mass part" may be simply given as "part" for convenience. The conversions and yields in the Examples and Comparative Examples are calculated by the following equations:

$$\text{Conversion [mol\%]} = \frac{\text{(Mol number of reacted starting material)}}{\text{(Mol number of fed starting material)}} \times 100$$

$$\text{Yield [mol \%]} = \frac{\text{(Mol number of unsaturated carboxylic acid formed)}}{\text{(Mol number of fed starting material)}} \times 100$$

Measurement of the Catalyst's Mechanical Strength

A stainless steel reaction pipe having an inner diameter of 25 mm and a length of 5000 mm was vertically set, and its lower end was sealed with a 1 mm-thick stainless steel receiver plate. About 50 g of a catalyst was weighed and dropped into the reaction pipe from the upper end of the pipe. Then the stainless steel receiver plate at the lower end of the reaction pipe was detached, and the catalyst was gently taken out of the reaction pipe. The catalyst so taken out was sifted with a sieve of a mesh size covering from 50 to 90% of the shorter of the standard diameter or length set for the catalyst grains and the mass(g) of the catalyst remaining on the sieve was weighed.

$$\text{Mechanical strength (mass \%)} = \frac{\text{(Mass (g) of catalyst remaining on the sieve)}}{\text{(Mass(g) of catalyst dropped from upper end of reaction pipe)}} \times 100$$

Measurement of the Catalyst's Attrition Loss

About 200 g of a catalyst was weighed and fed into a cylindrical drum-formed stainless steel air-tight vessel having a circular cross-section of 150 mm in diameter in the perpendicular direction and a horizontal width of 150 mm. The vessel was rotated centering around its horizontal center axis at 150 rpm for 30 minutes. Thereafter the catalyst was taken out and sifted with a sieve of a mesh size covering from 10 to 50% of the shorter of the standard diameter or length set for the catalyst grains and the mass(g) of the catalyst remaining on the sieve was weighed.

$$\text{Attrition loss (mass \%)} = \frac{\text{(Mass (g) of catalyst fed into vessel)} - \text{(Mass (g) of catalyst remaining on sieve)}}{\text{Mass (g) of catalyst fed into vessel]}} \times 100$$

Example 1

Catalyst Preparation

In 10,000 parts of purified water, 1,000 parts of ammonium molybdate, 331 parts of ammonium metavanadate and 229 parts of ammonium paratungstate were dissolved under heating and stirring. Separately, 342 parts of copper nitrate was dissolved in 1,000 parts of purified water under heating and stirring. Thus obtained two aqueous solutions were mixed, and to which 17 parts of antimony trioxide and 452 parts of titanium oxide were added, whereby providing a starting material liquid mixture. Adding thereto a SiC whisker having an average diameter of 0.8 μm and an average length of 40 μm, in an amount of 15 mass % to the catalytically active component, and a silica-alumina fiber having an average diameter of 2 μm and an average length of 100 μm in an amount of 15 mass % to the catalytically active component, a slurry was obtained. The slurry was dried with a spray dryer and then pulverized to 500 μm to provider a dry material. Injecting into the rotatory dish of a dish-type tumbling granulation machine, first 5,000 parts of a silica-alumina carrier having an average diameter of 5.0 mm and then gradually injecting the dry material together with 10 mass % of aqueous ethylene glycol solution as the binder, while continuously rotating the dish, the dry material was supported on the carrier. The resultant was calcined at 400° C. for 6 hours in an atmosphere of air, to provide Catalyst 1. The supporting ratio of this Catalyst 1 was about 30 mass %, and the composition of the metal elements in the catalytically active component except oxygen was as follows:

Mo$_{12}$V$_{6.0}$W$_{1.8}$Cu$_{3.0}$Sb$_{0.25}$Ti$_{12}$      Catalyst 1

The supporting ratio was determined following the equation below:

$$\text{Supporting ratio (mass \%)} = \frac{\text{Mass (g) of supported catalyst powder}}{\text{Mass (g) of carrier used}} \times 100.$$

The mechanical strength of this Catalyst 1 was measured with a sieve of 5 mm-mesh, and the attrition loss, with a sieve of 2 mm-mesh. The mechanical strength and attrition loss of this Catalyst 1 were as shown in Table 1.

Reactor

A reactor formed of a steel reaction tube of 3,000 mm in total length and 25 mm in inner diameter, and a shell covering the reaction tube for passing a heating medium therethrough was installed in vertical direction. Catalyst 1 was dropped thereinto from an upper part of the reaction tube to pack the latter up to the layer length of 2,800 mm.

Oxidation Reaction

From a lower part of the Catalyst 1-packed reaction tube, a feedstock gas, which was a mixture of 4 vol % of acrolein, 4 vol % of oxygen, 20 vol % of steam and the balance vol % of nitrogen, was introduced at a space velocity of 2,000 hr$^{-1}$ (STP), to carry out vapor-phase oxidation of acrolein. In that occasion, the temperature of the heating medium (the reaction temperature) was adjusted to make the acrolein conversion about 98 mol %. The results were as shown in Table 2.

Comparative Example 1

Example 1 was repeated except that the silica-alumina fiber having an average diameter of 2 μm and an average length of 100 μm was not added, to provide Catalyst 2. The supporting ratio and composition of the metal elements in the catalytically active component of this Catalyst 2 excluding oxygen were the same to those of Catalyst 1. The mechanical strength and attrition loss of Catalyst 2 were as shown in Table 1. This Catalyst 2 was packed in the reactor in the manner similar to Example 1, and the oxidation was conducted under identical conditions. The results were as given in Table 2.

Comparative Example 2

Example 1 was repeated except that the SiC whisker having an average diameter of 0.8 μm and average length of 40 μm was not added, to provide Catalyst 3. The supporting ratio and composition of the metal elements in the catalytically active component of this Catalyst 3 excluding oxygen were the same to those of Catalyst 1. The mechanical strength and attrition loss of Catalyst 3 were as shown in Table 1. This Catalyst 3 was packed in the reactor in the manner similar to Example 1, and acrolein oxidation was conducted under identical conditions. The results were as given in Table 2.

Example 2

Example 1 was repeated except that 10 mass % to the catalytically active component of a SiC whisker having an average diameter of 0.6 μm and average length of 30 μm was used instead of 15 mass % to the catalytically active component of the SiC whisker having an average diameter of 0.8 μm and average length of 40 μm; and that 10 mass % to the catalytically active component of a silica-alumina fiber having an average diameter of 3 μm and average length of 150 μm was used instead of 15 mass % to the catalytically active component of the silica-alumina fiber having an average diameter of 2 μm and average length of 100 μm, to provide Catalyst 4. The supporting ratio and composition of the metal elements in the catalytically active component of this Catalyst 4 excluding oxygen were the same to those of Catalyst 1. The mechanical strength of Catalyst 4 was measured with a sieve of 5-mm mesh, and the attrition loss, with a sieve of 2-mm mesh. The mechanical strength and attrition loss of Catalyst 4 were as given in Table 1. This Catalyst 4 was packed in the reactor in the manner similar to Example 1, and oxidation of acrolein was conducted under identical conditions. The results were as given in Table 2.

Example 3

Catalyst Preparation

In 10,000 parts of purified water, 1,000 parts of ammonium molybdate, 221 parts of ammonium metavanadate and 191 parts of ammonium paratungstate were dissolved under heating and stirring. Separately, 285 parts of copper nitrate and 69 parts of cobalt nitrate were dissolved in 1,000 parts of purified water under heating and stirring. Thus obtained two aqueous solutions were mixed, and to which 69 parts of antimony trioxide was added, to provide a starting material liquid mixture. The starting material liquid mixture was dried with a spray dryer and then pulverized to 500 μm, to provide a dry material. To the dry material, 5 mass % to the catalytically active component of a SiC whisker having an average diameter of 0.8 μm and average length of 40 μm and 5 mass % to the catalytically active component of an alumina fiber having an average diameter of 5 μm and average length of 200 μm were added, and mixed to provide a powder to be supported. Injecting into the rotatory dish of a dish-type tumbling granulation machine, first 3,500 parts of a silica-alumina carrier having an average diameter of 5.0 mm and then gradually injecting the powder to be supported, together with 10 mass % of aqueous ethylene glycol solution as the binder, while continuously rotating the dish, the powder was supported on the carrier. Thereafter the resultant was calcined at 400° C. for 6 hours in an atmosphere of air, to provide Catalyst 5. The supporting ratio of this Catalyst 5 was about 30 mass %, and the composition of the metal elements in the catalytically active component excepting oxygen was as follows:

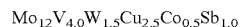

$Mo_{12}V_{4.0}W_{1.5}Cu_{2.5}Co_{0.5}Sb_{1.0}$     Catalyst 5

The mechanical strength of this Catalyst 5 was measured with a sieve of 5 mm-mesh, and the attrition loss, with a sieve of 2 mm-mesh. The mechanical strength and attrition loss of this Catalyst 5 were as shown in Table 1. This Catalyst 5 was packed in the reactor in the manner similar to Example 1, and oxidation of acrolein was conducted under identical conditions. The results were as given in Table 2.

Example 4

Example 3 was repeated expect that 5 mass % to the catalytically active component of a silica-alumina fiber having an average diameter of 6 μm and average length of 250 μm was used instead of 5 mass % to the catalytically active component of the alumina fiber having an average diameter of 5 μm and average length of 200 μm, to provide Catalyst 6. The supporting ratio of this Catalyst 6 and composition of the metal elements of its catalytically active component excepting oxygen were the same to those of Catalyst 5. The mechanical strength and attrition loss of Catalyst 6 were as given in Table 1. This Catalyst 6 was packed in the reactor in the manner similar to Example 1, and oxidation of acrolein was conducted under identical conditions. The results were as given in Table 2.

Comparative Example 3

Example 3 was repeated except that 5 mass % to the catalytically active component of a glass fiber having an average diameter of 10 μm and average length of 300 μm was used instead of 5 mass % to the catalytically active component of the alumina fiber having an average diameter of 5 μm and average length of 200 μm, to provide Catalyst 7. The supporting ratio of this Catalyst 7 and composition of the metal elements of its catalytically active component excepting oxygen were the same to those of Catalyst 5. The mechanical strength and attrition loss of Catalyst 7 were as given in Table 1. This Catalyst 7 was packed in the reactor in the manner similar to Example 1, and oxidation of acrolein was conducted under identical conditions. The results were as given in Table 2.

Comparative Example 4

Example 3 was repeated except that 5 mass % to the catalytically active component of a glass fiber having an average diameter of 20 μm and average length of 500 μm was used instead of 5 mass % to the catalytically active component of the alumina fiber having an average diameter of 5 μm and average length of 200 μm, to provide Catalyst 8. The supporting ratio of this Catalyst 8 and composition of the metal elements of its catalytically active component excepting oxygen were the same to those of Catalyst 5. The mechanical strength and attrition loss of Catalyst 8 were as given in Table 1. This Catalyst 8 was packed in the reactor in the manner similar to Example 1, and oxidation of acrolein was conducted under identical conditions. The results were as given in Table 2.

inorganic fibers, are supported on an inert carrier, and which is characterized in that it comprises as the inorganic fibers at least an inorganic fiber having an average diameter less than 1.0 μm and another inorganic fiber having an average diameter ranging from 1.5 to 7 μm.

2. A catalyst according to claim 1, in which the total content of the inorganic fibers ranges from 0.5 to 30 mass % to the catalytically active component.

3. A catalyst according to claim 1, in which the catalytically active component is a complex oxide represented by the following general formula (1):

$$Mo_{12}V_aA_bB_cC_dD_eO_x \qquad (1)$$

(wherein Mo is molybdenum; V is vanadium; A is at least an element selected from tungsten and niobium; B is at least an element selected from chromium, manganese, iron, cobalt, nickel, copper, zinc and bismuth; C is at least an element selected from antimony, tin, tellurium and phosphorus; D is at least an element selected from silicon, aluminium, titanium, cerium and zirconium; and O is oxygen; a, b, c, d, e and x stand for the respective atomic ratios of V, A, B, C, D and O, where $0<a\leq14$, $0\leq b\leq12$, $0\leq c\leq6$, $0\leq d\leq6$ and $0\leq e\leq50$, and x is a numerical value determined by the oxidized state of each of the elements).

TABLE 1

| | Catalyst No. | Inorganic Fiber-1 | | | | Inorganic Fiber-2 | | | | Mechanical Strength (mass %) | Attrition Loss (mass %) |
| --- | --- | --- | --- | --- | --- | --- | --- | --- | --- | --- | --- |
| | | Material | Diameter (μm) | Length (μm) | Content (mass %) | Material | Diameter (μm) | Length (μm) | Content (mass %) | | |
| Example 1 | Catalyst 1 | SiC whisker | 0.8 | 40 | 15 | silica-alumina | 2 | 100 | 15 | 99.7 | 1.5 |
| Comparative Example 1 | Catalyst 2 | SiC whisker | 0.8 | 40 | 15 | — | — | — | — | 95.2 | 3.7 |
| Comparative Example 2 | Catalyst 3 | — | — | — | — | silica-alumina | 2 | 100 | 15 | 98.8 | 8.3 |
| Example 2 | Catalyst 4 | SiC whisker | 0.6 | 30 | 10 | silica-alumina | 3 | 150 | 10 | 99.8 | 1.3 |
| Example 3 | Catalyst 5 | SiC whisker | 0.8 | 40 | 5 | alumina | 5 | 200 | 5 | 99.5 | 2.2 |
| Example 4 | Catalyst 6 | SiC whisker | 0.8 | 40 | 5 | alumina | 6 | 250 | 5 | 99.3 | 2.6 |
| Comparative Example 3 | Catalyst 7 | SiC whisker | 0.8 | 40 | 5 | glass | 10 | 300 | 5 | 97.9 | 4.4 |
| Comparative Example 4 | Catalyst 8 | SiC whisker | 0.8 | 40 | 5 | glass | 20 | 500 | 5 | 95.4 | 4.1 |

TABLE 2

| | Catalyst No. | Reaction Temp. (° C.) | Acrolein Conversion (mol %) | Acrylic Acid Selectivity (mol %) | Acrylic Acid Yield (mol %) |
| --- | --- | --- | --- | --- | --- |
| Example 1 | Catalyst 1 | 270 | 98.0 | 94.9 | 93.0 |
| Comparative Example 1 | Catalyst 2 | 275 | 98.0 | 94.5 | 92.6 |
| Comparative Example 2 | Catalyst 3 | 276 | 98.0 | 94.6 | 92.7 |
| Example 2 | Catalyst 4 | 268 | 98.1 | 95.0 | 93.2 |
| Example 3 | Catalyst 5 | 271 | 98.1 | 94.8 | 93.0 |
| Example 4 | Catalyst 6 | 272 | 98.1 | 94.7 | 92.9 |
| Comparative Example 3 | Catalyst 7 | 275 | 98.0 | 94.3 | 92.4 |
| Comparative Example 4 | Catalyst 8 | 277 | 97.9 | 94.2 | 92.2 |

The invention claimed is:

1. A catalyst for production of unsaturated carboxylic acid in which the catalytically active component comprising molybdenum and vanadium as the essential ingredients, and 4. A process for producing unsaturated carboxylic acid by catalytic vapor-phase oxidation of unsaturated aldehyde or saturated hydrocarbon in the presence of molecular oxygen, which uses a catalyst according to claim 1.

5. A catalyst according to claim 2, in which the catalytically active component is a complex oxide represented by the following general formula (1):

$$Mo_{12}V_aA_bB_cC_dD_eO_x \qquad (1)$$

(wherein Mo is molybdenum; V is vanadium; A is at least an element selected from tungsten and niobium; B is at least an element selected from chromium, manganese, iron, cobalt, nickel, copper, zinc and bismuth; C is at least an element selected from antimony, tin, tellurium and phosphorus; D is at least an element selected from silicon, aluminium, titanium, cerium and zirconium; and O is oxygen; a, b, c, d, e and x stand for the respective atomic ratios of V, A, B, C, D and O, where $0<a\leq14$, $0\leq b\leq12$, $0\leq c\leq6$, $0\leq d\leq6$ and $0\leq e\leq50$, and x is a numerical value determined by the oxidized state of each of the elements).

6. A process for producing unsaturated carboxylic acid by catalytic vapor-phase oxidation of unsaturated aldehyde or saturated hydrocarbon in the presence of molecular oxygen, which uses a catalyst according to claim 2.

7. A process for producing unsaturated carboxylic acid by catalytic vapor-phase oxidation of unsaturated aldehyde or saturated hydrocarbon in the presence of molecular oxygen, which uses a catalyst according to claim 3.

8. A process for producing unsaturated carboxylic acid by catalytic vapor-phase oxidation of unsaturated aldehyde or saturated hydrocarbon in the presence of molecular oxygen, which uses a catalyst according to claim 5.

* * * * *